United States Patent
Niwa et al.

(10) Patent No.: US 10,822,292 B2
(45) Date of Patent: Nov. 3, 2020

(54) METHOD FOR PRODUCING REACTION PRODUCT

(71) Applicant: NGK INSULATORS, LTD., Nagoya (JP)

(72) Inventors: Kousuke Niwa, Niwa-Gun (JP); Yoshio Kondo, Nagoya (JP); Hiroaki Isobe, Nagoya (JP); Michiro Aoki, Oobu (JP)

(73) Assignee: NGK Insulators, Ltd., Nagoya (JP)

(*) Notice: Subject to any disclaimer, the term of this patent is extended or adjusted under 35 U.S.C. 154(b) by 0 days.

(21) Appl. No.: 16/254,957

(22) Filed: Jan. 23, 2019

(65) Prior Publication Data

US 2019/0152881 A1 May 23, 2019

Related U.S. Application Data

(63) Continuation of application No. PCT/JP2017/028051, filed on Aug. 2, 2017.

(30) Foreign Application Priority Data

Aug. 3, 2016 (JP) .................... 2016-152522

(51) Int. Cl.
*C07C 17/08* (2006.01)
*C07C 19/075* (2006.01)
(Continued)

(52) U.S. Cl.
CPC ............ *C07C 17/08* (2013.01); *B01J 19/128* (2013.01); *C07C 17/02* (2013.01); *C07C 19/075* (2013.01);
(Continued)

(58) Field of Classification Search
CPC ....... C07C 17/08; C07C 17/02; C07C 19/075; H05B 3/26; H05B 3/03; H05B 3/10; G01N 21/35; B01J 19/128
(Continued)

(56) References Cited

U.S. PATENT DOCUMENTS

| 2003/0226996 A1 | 12/2003 | Aramaki et al. | |
| 2017/0269267 A1* | 9/2017 | Guha | G01N 21/35 |
| 2019/0194101 A1* | 6/2019 | Niwa | B01J 19/12 |

FOREIGN PATENT DOCUMENTS

| JP | 57-200273 A | 12/1982 |
| JP | 08-138841 A | 5/1996 |

(Continued)

OTHER PUBLICATIONS

Derwent abstract of JP 2015-198063 (Year: 2015).*

(Continued)

*Primary Examiner* — Luan V Van
*Assistant Examiner* — Colleen M Raphael
(74) *Attorney, Agent, or Firm* — Burr & Brown, PLLC (57) ABSTRACT

A method for producing a reaction product, with which the reaction product is obtained from a starting material through a particular organic synthesis reaction, the method includes (a) a step of setting a target wavelength to a peak wavelength of a reaction region involved in the organic synthesis reaction in an infrared absorption spectrum of the starting material; (b) a step of preparing an infrared heater that emits an infrared ray having a peak at the target wavelength from a structure constituted by a metal pattern, a dielectric layer, and a metal substrate stacked in this order from an outer side toward an inner side; and (c) a step of obtaining the reaction product by allowing the organic synthesis reaction to proceed while the infrared ray having a peak at the target wavelength is being applied to the starting material from the infrared heater.

8 Claims, 3 Drawing Sheets

(51) Int. Cl.
- *G01N 21/35* (2014.01)
- *H05B 3/10* (2006.01)
- *B01J 19/12* (2006.01)
- *C07C 17/02* (2006.01)
- *H05B 3/03* (2006.01)
- *H05B 3/26* (2006.01)

(52) U.S. Cl.
CPC ............ *G01N 21/35* (2013.01); *H05B 3/03* (2013.01); *H05B 3/10* (2013.01); *H05B 3/26* (2013.01)

(58) Field of Classification Search
USPC .......................................... 204/157.6–158.21
See application file for complete search history.

(56) References Cited

FOREIGN PATENT DOCUMENTS

| | | |
|---|---|---|
| JP | 2003-304014 A | 10/2003 |
| JP | 2006-140377 A | 6/2006 |
| JP | 2017-050254 A | 3/2017 |
| WO | 2007/052778 A1 | 5/2007 |

OTHER PUBLICATIONS

English translation of International Preliminary Report on Patentability (Chapter I) (Application No. PCT/JP2017/028051) dated Feb. 14, 2019, 7 pages.

International Search Report (with English translation) and Written Opinion (Application No. PCT/JP2017/028051) dated Aug. 29, 2017.

Fugami, Keigo, "*Birth of Selective Organic Synthesis Chemistry Involving Mid-Infrared Pulse Laser Light*," [online] Grants-in-Aid for Scientific Research Database, 2006 Annual Research Report, May 7, 2008, https://kaken.nii.ac.jp/ja/report/KAKENHI-PROJECT-18655036/RECORD-186550362006jisseki/.

Fugami, Keigo, "*Birth of Selective Organic Synthesis Chemistry Involving Mid-Infrared Pulse Laser Light*," [online] Grants-in-Aid for Scientific Research Database, KAKEN 2007 Annual Research Report, Feb. 3, 2010, https://kaken.nii.ac.jp/ja/report/KAKENHI-PROJECT-18655036/RECORD-186550362007jisseki/.

Sakurai, Atsushi, "*Thermal Radiation Control by Metamaterial*," National Heat Transfer Symposium of Japan Koen Ronbunshu, 2014, vol. 51st, H344.

Fugami, Keigo, et al., "*Selective C—O Bond Activation by Means of Mid-IR Pulse Laser Irradiation*," Symposium on Physical Organic Chemistry Yoshishu, 2009, vol. 2009, p. 352.

\* cited by examiner

METHOD FOR PRODUCING REACTION PRODUCT

BACKGROUND OF THE INVENTION

1. Field of the Invention

The present invention relates to a method for producing a reaction product.

2. Description of the Related Art

Studies have been made on the use of infrared pulsed laser light in a novel approach to organic synthesis reactions. For example, NPL 1 reports that an attempt was made to perform rearrangement reactions on propene oxide and 1-butene oxide by irradiation with 984 $cm^{-1}$ and 916 $cm^{-1}$ infrared pulsed laser light, and that both oxides were converted into corresponding aldehydes after irradiation for 40 minutes. NPL 2 reports that, in a carbon-nitrogen bond cleavage reaction by irradiation with mid-infrared pulsed laser light, diisopropylethylamine could be quantitively consumed by irradiation with a pulsed laser having a wavelength of 6.96 μm and that diisopropylamine could be quantitively reacted by irradiation with a pulsed laser having a wavelength of 8.33 μm.

CITATION LIST

Patent Literature

NPL 1: FUGAMI, Keigo "Birth of selective organic synthesis chemistry involving mid-infrared pulse laser light" [on line] May 7, 2008, Grants-in-Aid for Scientific Research Database, 2006 Annual Research Report [searched Jul. 11, 2016], internet <URL: https://kaken.nii.ac.jp/ja/report/KAKENHI-PROJECT-18655036/RECORD-186550362006jisseki/>

NPL 2: FUGAMI, Keigo "Birth of selective organic synthesis chemistry involving mid-infrared pulse laser light" [on line] Feb. 3, 2010, Grants-in-Aid for Scientific Research Database, KAKEN 2007 Annual Research Report [searched Jul. 11, 2016], internet, <URL: https://kaken.nii.ac.jp/ja/report/KAKENHI-PROJECT-18655036/RECORD-186550362007jisseki/>

SUMMARY OF THE INVENTION

However, since the infrared wavelength of the infrared pulsed laser light is determined by a laser medium, there has been a problem in that the wavelength could not be set as desired. Thus, only limited starting materials could be used, and the versatility was low.

The present invention has been made to address such a problem, and a main object thereof is to provide a method for obtaining a reaction product through a particular organic synthesis reaction while irradiating a starting material with an infrared ray, with which a wide variety of starting materials can be used.

A method for producing a reaction product according to the present invention is a method with which the reaction product is obtained from a starting material through a particular organic synthesis reaction, the method including:

(a) a step of setting a target wavelength to a peak wavelength of a reaction region involved in the organic synthesis reaction in an infrared absorption spectrum of the starting material;

(b) a step of preparing an infrared heater that emits an infrared ray having a peak at the target wavelength from a structure constituted by a metal pattern, a dielectric layer, and a metal substrate stacked in this order from an outer side toward an inner side; and (c) a step of obtaining the reaction product by allowing the organic synthesis reaction to proceed while the infrared ray having a peak at the target wavelength is being applied to the starting material from the infrared heater.

In this method, an infrared heater that emits an infrared ray, which has a peak at a particular wavelength, from a structure constituted by a metal pattern, a dielectric layer, and a metal substrate stacked in this order from an outer side toward an inner side is used. Such an infrared heater can be designed so that the peak wavelength of the emitted infrared ray accurately corresponds to the target wavelength. Thus, when the target wavelength is set to a peak wavelength of a reaction region involved in the organic synthesis reaction in an infrared absorption spectrum of the starting material, the infrared heater can be designed to emit an infrared ray that has a peak at that target wavelength. Moreover, a reaction product can be efficiently obtained by allowing the organic synthesis reaction to proceed while irradiating the starting material with an infrared ray having a peak at the target wavelength. Thus, according to the present invention, the method for obtaining a reaction product through a particular organic synthesis reaction while irradiating a starting material with an infrared ray can be applied to a wide variety of starting materials.

DETAILED DESCRIPTION OF THE INVENTION

Preferred embodiments of the present invention will now be described.

A method for producing a reaction product according to this embodiment is a method with which the reaction product is obtained from a starting material through a particular organic synthesis reaction, the method including:

(a) a step of setting a target wavelength to a peak wavelength of a reaction region involved in the organic synthesis reaction in an infrared absorption spectrum of the starting material;

(b) a step of preparing an infrared heater that emits an infrared ray having a peak at the target wavelength from a structure constituted by a metal pattern, a dielectric layer, and a metal substrate stacked in this order from an outer side toward an inner side; and (c) a step of obtaining the reaction product by allowing the organic synthesis reaction to proceed while the infrared ray having a peak at the target wavelength is being applied to the starting material from the infrared heater.

In the method of this embodiment, there may be one starting material or two or more starting materials. For example, in intramolecular reactions and intermolecular reactions between identical molecules, one starting material is used. Two or more starting materials are used for intermolecular reactions between dissimilar molecules.

In the method of this embodiment, in step (a), the target wavelength is set to a peak wavelength of a reaction region involved in the organic synthesis reaction in an infrared absorption spectrum of the starting material.

For example, when the particular organic synthesis reaction is an intramolecular dehydration reaction, an alcohol compound in which a hydroxy group and a hydrogen atom are respectively present at two carbon atoms that are adjacent to each other within one molecule is used as a starting material, and an olefin compound is obtained through dehydration involving the hydroxy group and the hydrogen atom. In this case, there is one starting material. Preferably, the target wavelength is set to a peak wavelength of the C—O region, which is the reaction region involved in the intramolecular dehydration reaction, in the infrared absorption spectrum the alcohol compound used as the starting material. The peak wavelength of the C—O stretching vibration is preferable as the peak wavelength of the C—O region. In general, the peak wavelength of the C—O stretching vibration of an alcohol compound is 1260 to 1000 $cm^{-1}$ (7.93 to 10.00 μm).

When the particular organic synthesis reaction is the rearrangement reaction described in NPL 1, an aldehyde compound is obtained by inducing a rearrangement reaction involving propene oxide, which is an epoxy compound, as the starting material. In this case also, there is one starting material. Preferably, the target wavelength is set to a peak wavelength of symmetric or asymmetric stretching of an epoxy ring, which is the reaction region involved in the rearrangement reaction, in the infrared absorption spectrum of the epoxy compound used as the starting material. In general, the peak wavelength of symmetric stretching of the epoxy ring of an epoxy compound is near 1250 $cm^{-1}$ (8.00 μm), and the peak wavelength of asymmetric stretching of the epoxy ring is 950 to 810 $cm^{-1}$ (10.53 to 12.35 μm).

When the particular organic synthesis reaction is an electrophilic addition reaction, an electrophilic addition compound is obtained by performing a reaction using an olefin compound and an electrophile (for example, hydrogen chloride) as starting materials. In this case, there are two starting materials, an olefin compound and an electrophile. Preferably, the target wavelength is set to a peak wavelength of the C=C region, which is the reaction region involved in the electrophilic addition reaction, in the infrared absorption spectrum of the olefin compound used as the starting material. The peak wavelength of the C=C stretching vibration is preferable as the peak wavelength of the C=C region. In general, the peak wavelength of the C=C stretching vibration of an olefin compound is 1660 to 1640 $cm^{-1}$ (6.00 to 6.10 μm).

In the method of this embodiment, in step (b), an infrared heater that emits an infrared ray, which has a peak at a target wavelength, from a structure constituted by a metal pattern, a dielectric layer, and a metal substrate stacked in this order from an outer side toward an inner side is used.

Figure 1:
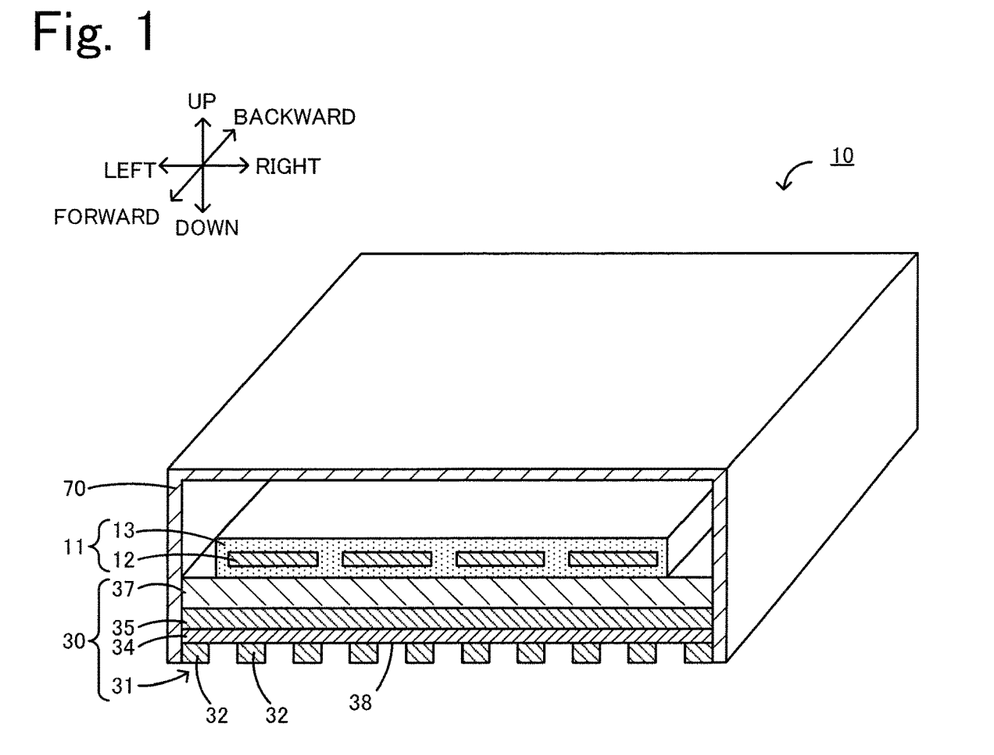
FIG. 1 is a perspective view of an infrared heater 10.
Figure 2:
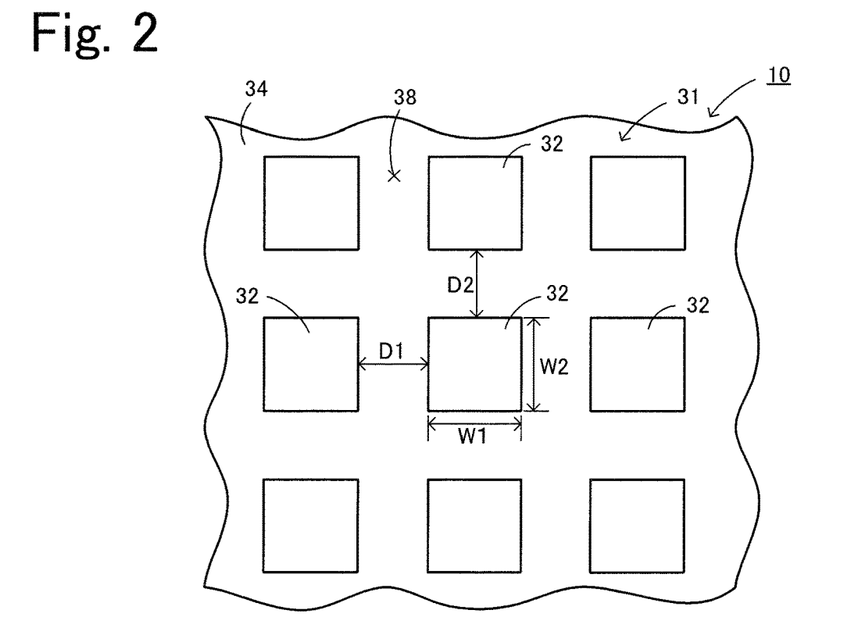
FIG. 2 is a partial bottom view of the infrared heater 10.

FIG. 1 is a perspective view of an infrared heater 10, a portion of which is shown as a cross-section. FIG. 2 is a partial bottom view of the infrared heater 10. The left-right directions, forward-backward directions, and up-down directions are as indicated in FIG. 1. The infrared heater 10 is equipped with a heater body 11, a structure 30, and a casing 70. The infrared heater 10 emits an infrared ray toward a subject disposed below not shown in the drawings.

The heater body 11 is configured as what is known as a plate heater, and is equipped with a heating element 12 formed of a wire member bent into a zigzag shape, and a protective member 13, which is an insulator that contacts the heating element 12 and surrounds the heating element 12. Examples of the material for the heating element 12 include W, Mo, Ta, Fe—Cr—Al alloys, and Ni—Cr alloys. Examples of the material for the protective member 13 include insulating resins, such as polyimide, and ceramics. The heater body 11 is installed inside the casing 70. Two ends of the heating element 12 are respectively connected to a pair of input terminals, not illustrated, attached to the casing 70. Power can be supplied from the exterior to the heating element 12 through this pair of input terminals. Alternatively, the heater body 11 may be a plate heater formed of a ribbon-shaped heating element wound around an insulator.

The structure 30 is a plate-shaped member disposed below the heating element 12. In the structure 30, a first conductor layer 31, a dielectric layer 34, a second conductor layer 35, and a support substrate 37 are stacked in this order from the outer side toward the inner side below the infrared heater 10. The structure 30 is disposed to cover the opening in the lower portion of the casing 70.

As illustrated in FIG. 2, the first conductor layer 31 is configured as a metal pattern having a periodic structure, in which metal electrodes 32 identical in size and shape are arranged to be equally spaced from one another on the dielectric layer 34. Specifically, the first conductor layer 31 is configured as a metal pattern in which multiple rectangular metal electrodes 32 are placed on the dielectric layer 34 so as to be equally spaced from each other by a distance D1 in the left-right directions and by a distance D2 in the forward-backward directions. The metal electrodes 32 are shaped such that the thickness (height in the up-down directions) is smaller than a sideways width W1 (width in the left-right directions) and a lengthways width W2 (width in the forward-backward directions). The period of the metal pattern in the sideways direction is Λ1=D1+W1, and the period in the lengthways direction is Λ2=D2+W2. Here, D1 equals D2, and W1 equals W2. Examples of the material for the metal electrodes 32 include gold and aluminum (Al). The metal electrodes 32 are bonded to the dielectric layer 34 via a bonding layer not illustrated in the drawings. Examples of the material for the bonding layer include chromium (Cr), titanium (Ti), and ruthenium (Ru).

The dielectric layer 34 is a plate-shaped member having an upper surface bonded to the second conductor layer 35. The dielectric layer 34 is sandwiched between the first conductor layer 31 and the second conductor layer 35. Of the lower surface of the dielectric layer 34, portions on which the metal electrodes 32 are not disposed serve as the emission surface 38 from which an infrared ray is emitted toward a subject. Examples of the material for the dielectric layer 34 include alumina ($Al_2O_3$) and silica ($SiO_2$).

The second conductor layer 35 is a metal plate having an upper surface bonded to the support substrate 37 via a bonding layer not shown in the drawings. Examples of the material for the second conductor layer 35 are the same as those for the first conductor layer 31. Examples of the material for the bonding layer include chromium (Cr), titanium (Ti), and ruthenium (Ru).

The support substrate 37 is a plate-shaped member fixed to the interior of the casing 70 with, for example, a fixture not shown in the drawings, and supports the first conductor layer 31, the dielectric layer 34, and the second conductor layer 35. Examples of the material for the support substrate 37 include materials which can easily maintain a flat and smooth surface, have high heat resistance, and undergo less thermal warping, such as a Si wafer and glass. The support substrate 37 may be in contact with the lower surface of the heater body 11 or may be separated in the up-down directions from the lower surface without making contact and with a space therebetween. When the support substrate 37 is in contact with the heater body 11, they may be bonded.

This structure 30 functions as a metamaterial emitter that has a property of selectively emitting an infrared ray of a particular wavelength. This property is considered to be due to a resonance phenomenon explained by magnetic polariton. Magnetic polariton is a resonance phenomenon in which a strong electromagnetic field confining effect is obtained in a dielectric (dielectric layer 34) between two conductor layers (the first conductor layer 31 and the second conductor layer 35) above and below the dielectric. As a result, of the dielectric layer 34 in the structure 30, the portions sandwiched between the second conductor layer 35 and the metal electrodes 32 serve as infrared ray emission sources. The infrared ray emitted from the emission sources circumvents the metal electrodes 32, and is emitted toward the ambient environment from the portions (that is, the emission surface 38) of the dielectric layer 34 on which no metal electrodes 32 are present. Moreover, according to this structure 30, the resonance wavelength can be adjusted by adjusting the materials for the first conductor layer 31, the dielectric layer 34, and the second conductor layer 35, and the shape and the periodic structure of the first conductor layer 31. As a result, the infrared ray emitted from the emission surface 38 of the structure 30 exhibits properties with which an emissivity of an infrared ray having a particular wavelength is high. In this embodiment, the materials, the shape, the periodic structure, etc., described above are adjusted so that the structure 30 has a property (hereinafter simply referred to as a "particular emission property") of emitting, from the emission surface 38, an infrared ray having a maximum peak, which has a full width at half maximum of 1.5 μm or less (preferably 1.0 μm or less) and an emissivity of 0.7 or more (preferably 0.8 or more), within a wavelength range of 0.9 μm or more and 25 μm or less (preferably 2.5 μm or more and 25 μm or less (4000 to 400 cm$^{-1}$)). In other words, the structure 30 has a property of emitting an infrared ray having a sharp maximum peak with a relatively small full width at half maximum and a relatively high emissivity.

Such a structure 30 can be produced as follows, for example. First, a bonding layer (not illustrated) and a second conductor layer 35 are formed sequentially in this order on a surface (lower surface in FIG. 1) of the support substrate 37 by sputtering. Next, a dielectric layer 34 is formed on a surface (lower surface in FIG. 1) of the second conductor layer 35 by an atomic layer deposition (ALD) method. Subsequently, after a predetermined resist pattern is formed on a surface (lower surface in FIG. 1) of the dielectric layer 34, a bonding layer (not illustrated) and a layer composed of a material for the first conductor layer 31 are sequentially formed by a helicon sputtering method. Then the resist pattern is removed to form a first conductor layer 31 (metal electrodes 32).

The casing 70 substantially has a shape of a cuboid with a space inside and an open bottom. The heater body 11 and the structure 30 are placed in the space inside the casing 70. The casing 70 is formed of a metal (for example, SUS or aluminum) so that the infrared ray emitted from the heating element 12 is reflected.

An example of the use of the infrared heater 10 is described below. First, power is supplied to the two ends of the heating element 12 via the input terminals from a power supply not illustrated in the drawings. Power is supplied so that the temperature of the heating element 12 reaches a preset temperature (this temperature is not particularly limited but is assumed to be 350° C. here). Energy from the heating element 12 reaching the preset temperature is transmitted to the surroundings through at least one three forms of heat transfer, i.e., conduction, convection, and radiation, and heats the structure 30. As a result, the structure 30 is heated to a particular temperature and serves as a secondary radiator that emits an infrared ray. At this stage, since the structure 30 includes the first conductor layer 31, the dielectric layer 34, and the second conductor layer 35 as described above, the infrared heater 10 emits an infrared ray on the basis of the particular emission properties.

Figure 3:
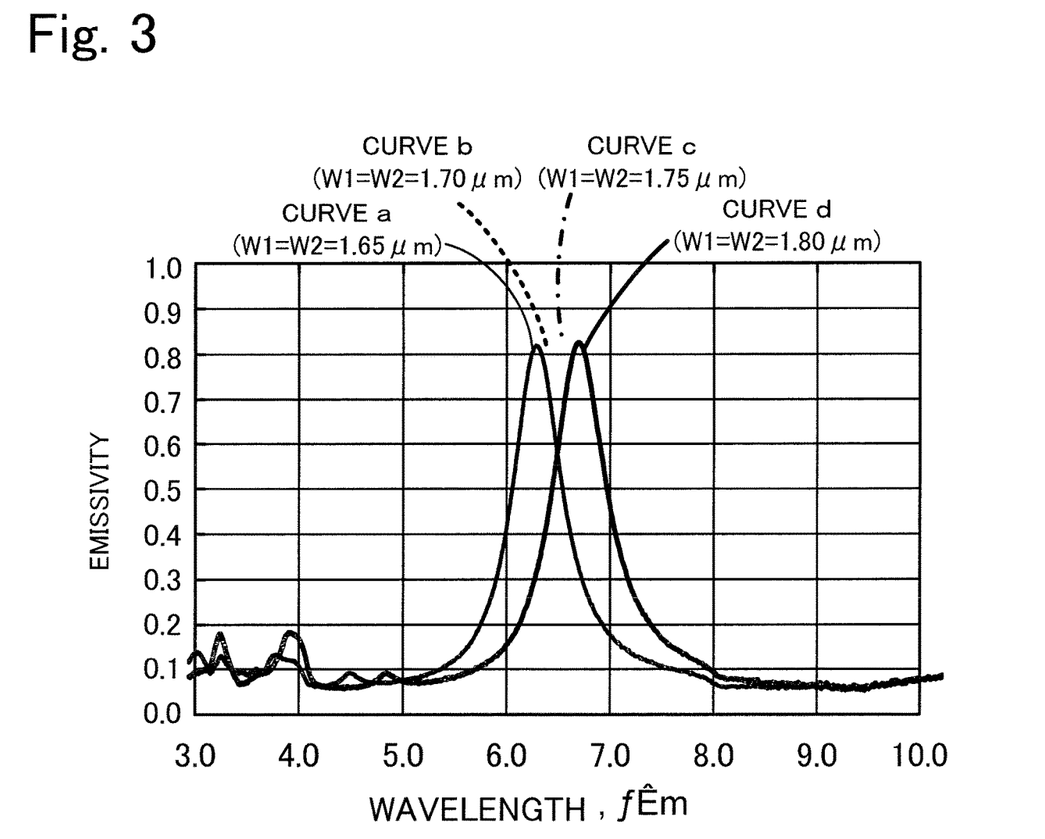
FIG. 3 is a graph showing one example of emission properties of infrared rays emitted from an emission surface 38.

FIG. 3 is a graph showing one example of emission properties of infrared rays emitted from the emission surface 38. The curves a to d shown in FIG. 3 are obtained by measuring the emissivity of the infrared ray from the emission surface 38 while varying the sideways width W1 and the lengthways width W2 of the metal electrodes 32, and plotting the measured values. The emissivity was measured as follows. First, the normal incidence hemispherical reflectance of the infrared ray from the emission surface 38 was measured with a Fourier transform-infrared spectroscope (FT-IR) equipped with an integrating sphere. Next, while assuming the transmittance to be 0, the value obtained by conversion using the formula, (emissivity)=1−(reflectivity), obtained by applying Kirchhoff's circuit laws was assumed to be the measured emissivity value. Note that all of the curves a to d indicate the results obtained by using gold in the first conductor layer 31 and the second conductor layer 35 and alumina in the dielectric layer 34 and setting the thickness of the first conductor layer 31 to 100 μm, the distance D1 and the distance D2 to 1.50 μm, the thickness of the dielectric layer 34 to 120 μm, and the temperature of the structure 30 to 200° C. The curve a (thin solid line), the curve b (chain line), the curve c (one-dot chain line), and the curve d (thick solid line) are profiles obtained by setting the sideways width W1 (=lengthways width W2) to 1.65 μm, 1.70 μm, 1.75 μm, and 1.80 μm, respectively. For all of the curves a to d, the full width at half maximum of the maximum peak was 1.5 μm or less and, even 1.0 μm or less, and the emissivity of the maximum peak exceeded 0.7 (=70%) and even exceeded 0.8 (=80%). It was found that as the width of the metal electrodes 32 increased from 1.65 μm to 1.85 μm, the peak wavelength (resonance wavelength) shifted toward the long wavelength side. The calculated values and the measured values of the peak wavelengths are shown in Table 1. The calculated values were the theoretically predicted values of the resonance wavelength using an LC circuit model. Table 1 shows that in general, good correspondence was found between the calculated values and the measured values. Here, the width of the metal electrodes 32 was changed with 0.05 μm increments, and the peak wavelength was generated with increments of few tenth of a micrometer. Thus, the peak wavelength can accurately correspond to the target wavelength. It can be predicted that when the width of the metal electrodes 32 is designed with 0.01 μm increments, the peak wavelength can be generated with increments of few tens of nanometers. In such a case, the peak wavelength can more accurately correspond to the target wavelength.

TABLE 1

| Width of the metal electrode | Peak wavelength (Resonance wavelength) | |
| --- | --- | --- |
| W1 (=W2) [μm] | Calculated value λ LC | Measured value λ exp |
| 1.65 | 6.13 μm (1631 cm$^{-1}$) | 6.29 μm (1590 cm$^{-1}$) |
| 1.70 | 6.32 μm (1582 cm$^{-1}$) | 6.39 μm (1565 cm$^{-1}$) |
| 1.75 | 6.50 μm (1538 cm$^{-1}$) | 6.54 μm (1529 cm$^{-1}$) |
| 1.80 | 6.69 μm (1495 cm$^{-1}$) | 6.69 μm (1495 cm$^{-1}$) |

In the method of this embodiment, in step (c), a reaction product is obtained by allowing the organic synthesis reaction to proceed while irradiating the starting material with an infrared ray having a peak at the target wavelength. Although the infrared heater 10 described above is designed to mainly emit the infrared ray having the target wavelength, it is difficult to eliminate all radiations other than the target wavelength from the infrared ray emitted from the structure 30, and, furthermore, convection heat dissipation is expected to occur from parts of the heater to the surroundings in an air atmosphere. Thus, in constructing an actual process, the shape of the device, etc., should be considered so that the raw materials and the like are not excessively heated due to the auxiliary heat flow such as this.

The reaction temperature may be appropriately set according to the reaction rate, etc. The reaction time may be appropriately set according to the starting material, the reaction temperature, etc. Furthermore, a catalyst that accelerates the organic synthesis reaction may be added as needed. The obtained reaction product can be isolated by a common isolating technique. For example, after the reaction solvent in the reaction mixture is condensed at a reduced pressure, the desired reaction product can be isolated by purification by column chromatography, recrystallization, or the like.

Figure 4:
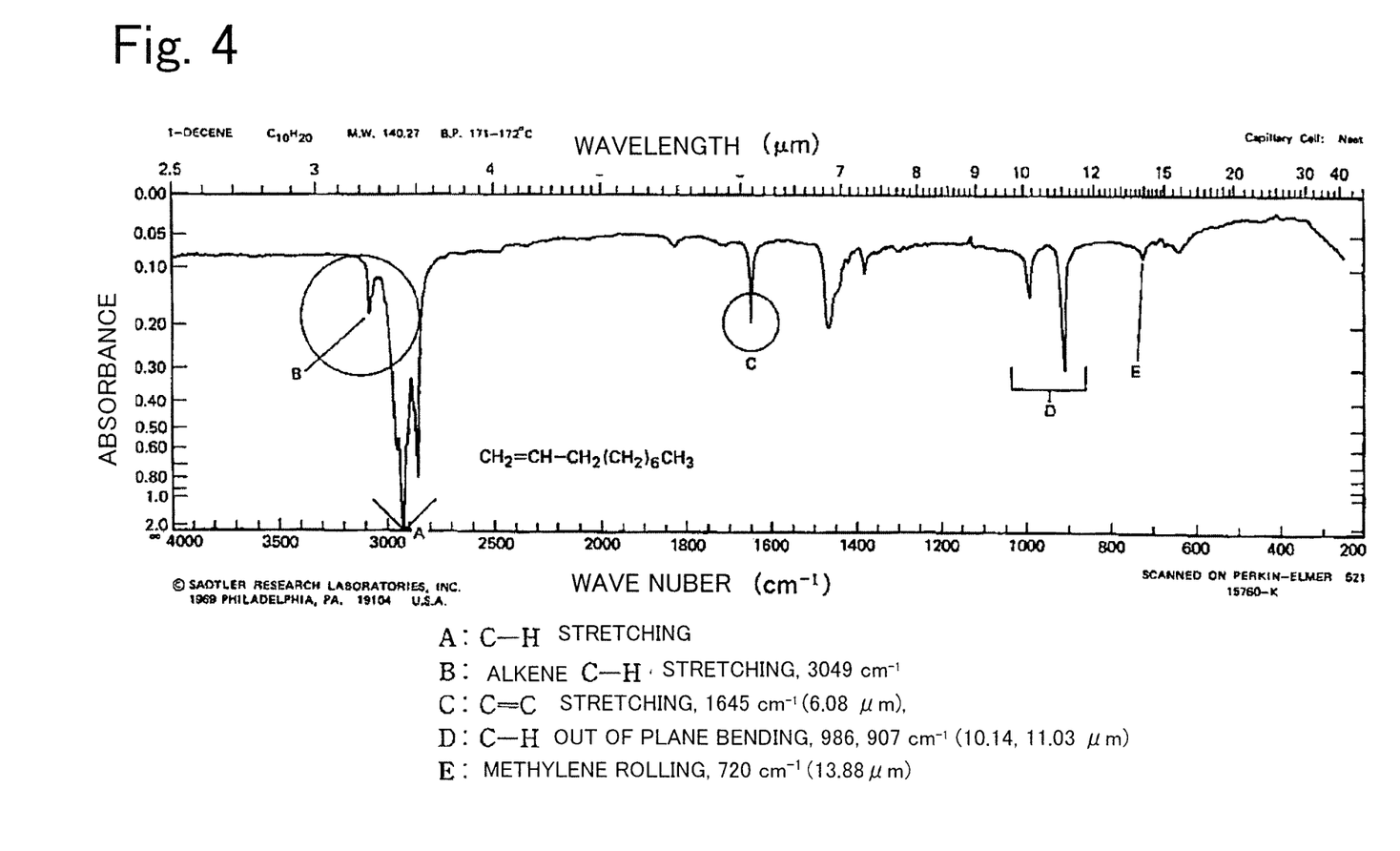
FIG. 4 is a graph showing an infrared absorption spectrum of 1-decene.

For example, one example of the scheme in which the organic synthesis reaction is the electrophilic addition reaction described above is shown in formula (1) below. In formula (1), 2-chiorodecane is obtained as a result of an electrophilic addition reaction between 1-decene and hydrogen chloride. The infrared absorption spectrum of 1-decene is shown in FIG. 4. In this case, the peak wavelength of stretching vibration of C=O, which is the reaction region involved in the electrophilic addition reaction of 1-decene, is 1645 cm$^{-1}$ (6.08 μm, see peak C in FIG. 4), and this wavelength is preferably set as the target wavelength. In the infrared heater described above, the widths (sideways width W1 and lengthways width W2) of square metal electrodes are accurately set so as to emit an infrared ray having this peak wavelength. Then the electrophilic addition reaction between 1-decene and hydrogen chloride is performed while irradiating 1-decene with an infrared ray from the infrared heater. Presumably, in this manner, due to the selective vibration excitation of the C=C region in 1-decene, a transition state is efficiently generated, and the reaction proceeds efficiently. Thus, a shorter reaction time and a lower reaction temperature can be anticipated. Moreover, such effects are obtained for a region, such as an aliphatic compound and an aromatic compound, having an interatomic π bond, and when an infrared ray is selectively applied with respect to the infrared absorption wavelength inherent to this region, already known reactions with various types of reagents can efficiently proceed. Furthermore, reactions which have been considered as difficult in the past can be performed by irradiation with an infrared ray of a particular wavelength.

[Chem. 1]

In the method of the this embodiment described in detail above, the infrared heater 10 that emits an infrared ray having a peak at a particular wavelength from the structure 30 that has absorbed energy from the heating element 12 is used. The infrared heater 10 can be designed so that the peak wavelength of the emitted infrared ray can accurately correspond to the target wavelength. Thus, the infrared heater 10 can be designed so that, when the target wavelength is set to a peak wavelength of a reaction region involved in the organic synthesis reaction in an infrared absorption spectrum of the starting material, an infrared ray that has a peak at that target wavelength is emitted. Moreover, the reaction product can be efficiently obtained by allowing the organic synthesis reaction to proceed while irradiating the starting material with an infrared ray having a peak at the target wavelength. Thus, according to this embodiment, the method for obtaining a reaction product through a particular organic synthesis reaction while irradiating a starting material with an infrared ray can be applied to a wide variety of starting materials.

In addition, the first conductor layer 31 is configured as a metal pattern having a periodic structure in which metal electrodes 32 identical in size and shape are arranged to be equally spaced from one another. According to the infrared heater 10, the peak wavelength of the emitted infrared ray changes depending on the sideways width W1 and the lengthways width W2 of the metal electrodes 32. The sideways width W1 and the lengthways width W2 of the metal electrodes 32 can be obtained accurately according to the designed values by performing lithography with a known electron beam lithographic device, and lift-off, for example.

In this manner, the operation of adjusting the peak wavelength of the infrared ray emitted from the infrared heater 10 to correspond to the target wavelength can be relatively easily performed with high accuracy.

Moreover, since the target wavelength is set within the wavelength range of 0.9 μm or more and 25 μm or less (preferably 2.5 μm or more and 25 μm or less (4000 to 400 $cm^{-1}$)), a typical infrared absorption spectrum measurement range can be covered.

It is needless to say that the present invention is not limited to the above-described embodiment, and that the present invention can be implemented in other various embodiments insofar as falling within the technical scope of the invention.

For example, in the embodiments described above, the intramolecular dehydration reaction, the rearrangement reaction, and the electrophilic addition reaction are described as the examples of the organic synthesis reaction; however, these examples are not limiting, and the present invention can be used in various organic synthesis reactions, such as a nucleophilic addition reaction and a nucleophilic substitution reaction. Examples of such an organic synthesis reaction include reactions performed on regions where π bonds are formed, and examples of such reactions include halogenation, deuteration, and addition of water performed on aliphatic compounds, such as polyolefins and unsaturated hydrocarbons, e.g., alkenes and alkynes, and on aromatic compounds, such as benzene ring structures, and hydrolyses of amide compounds and ester compounds.

In the embodiments described above, the metal electrodes 32 have a rectangular shape, but the shape is not limited to this. For example, the metal electrodes 32 may have a circular shape or a cross shape (shape formed of rectangles intersecting each other perpendicularly). When the metal electrodes 32 have a circular shape, the diameter of the circle corresponds to the sideways width W1 and the lengthways width W2, and when the metal electrodes 32 have a cross shape, the lengths of long sides of the two intersecting rectangles respectively correspond to the sideways width W1 and the lengthways width W2. Moreover, although the metal electrodes 32 are arranged in a grid pattern and equally spaced from one another in the left-right directions and the forward-backward directions, the arrangement is not limited to this. For example, the metal electrodes 32 may be arranged to be equally spaced from one another in the left-right directions only or the forward-backward directions only.

In the embodiments described above, the structure 30 is equipped with the support substrate 37; however, the support substrate 37 may be omitted. In the structure 30, the first conductor layer 31 may be directly bonded to the dielectric layer 34 without a bonding layer, and/or the second conductor layer 35 may be directly bonded to the support substrate 37 without a bonding layer.

EXAMPLES

Example 1

To a reactor, 62.8 mL of 1-hexene (0.5 mol, produced by Tokyo Chemical Industry Co., Ltd.) was added, and the reactor was purged with Ar gas for 15 minutes. Subsequently, while the reactor was cooled (−20° C.), irradiation with a 1600 to 1700 $cm^{-1}$ infrared ray having a peak at 1650 $cm^{-1}$ was started from above the reactor (5 W: irradiation energy per infrared ray-irradiated area of 3 cm square/unit area: about 0.5 $W/cm^2$) was started. Subsequently, hydrogen bromide gas (TAIYO NIPPON SANSO CORPORATION) was introduced to 1-hexene under stirring under a condition of 0.21 mol/hr. Introduction of the gas was halted 30 minutes, 1 hour, 2 hours, and 3 hours after the introduction of the hydrogen bromide gas, the interior of the reactor was substituted with Ar gas, and each reaction solution was stored at −196° C.

Comparative Example 1

To a reactor, 62.8 mL of 1-hexene (0.5 mol, produced by Tokyo Chemical Industry Co., Ltd.) was added, and the reactor was purged with Ar gas for 15 minutes. Subsequently, the reactor was cooled (−20° C.), and hydrogen bromide gas (produced by TAIYO NIPPON SANSO CORPORATION) was introduced to 1-hexene under stirring under a condition of 0.21 mol/hr. Introduction of the gas was halted 30 minutes, 1 hour, 2 hours, and 3 hours after the introduction of the hydrogen bromide gas, the interior of the reactor was substituted with Ar gas, and each reaction solution was stored at −196° C.

NMR measurement was performed on reaction solutions of Example 1 and Comparative Example 1 for each reaction time, and also on 1-hexene used as the raw material. From the results, the amounts of 1-hexene and 2-bromohexane in terms of % by weight contained in the reaction solutions were determined for each reaction time. The results are shown in Table 2.

TABLE 2

|  |  | Example 1 | | Comparative Example 1 | |
| --- | --- | --- | --- | --- | --- |
|  |  | 1-hexene (wt %) | 2-bromo-hexane (wt %) | 1-hexene (wt %) | 2-bromo-hexane (wt %) |
|  | Material | 100 | 0 | 100 | 0 |
| Reaction Time | 30 minutes later | 76 | 20 | 85 | 13 |
|  | 1 hour later | 48 | 43 | 67 | 28 |
|  | 2 hours later | 31 | 59 | 53 | 40 |
|  | 3 hours later | 8 | 80 | 30 | 52 |

It could be confirmed from Table 2 that, in Example 1 in which irradiation with a 1600 to 1700 $cm^{-1}$ infrared ray having a peak at 1650 $cm^{-1}$ was performed and Comparative Example 1 in which such irradiation was not performed, the reaction from 1-hexene to 2-bromohexane proceeded faster in Example 1. This result showed that a reaction product could be efficiently obtained by allowing the organic synthesis reaction to proceed while irradiating the starting material with an infrared ray having a peak at the target wavelength.

Example 2

To a reactor, 0.25 mol of 1-octene (39.2 mL, produced by Tokyo Chemical Industry Co., Ltd.), 0.025 mol of tributylhexadecylphosphonium bromide (12.7 g, produced by Tokyo Chemical Industry Co., Ltd.), and 3.75 mol of an aqueous HCl solution (40 mL) were added, and the reactor was purged with Ar gas for 15 minutes. Subsequently, the reactor was placed in an oil bath (115° C.), irradiation with a 1580 to 1680 $cm^{-1}$ infrared ray having a peak at 1630 $cm^{-1}$ was started from above the reactor (above the organic phase) (5 W: irradiation energy per infrared ray-irradiated area of 3 cm square/unit area: about 0.5 $W/cm^2$) was started, and the mixture solution was stirred to start the reaction. Twenty five hours after the start of the reaction, irradiation with the infrared ray and stirring were stopped, and the reactor was removed from the oil bath to terminate the reaction.

Comparative Example 2

To a reactor, 0.25 mol of 1-octene (39.2 mL, produced by Tokyo Chemical Industry Co., Ltd.), 0.025 mol of tributylhexadecylphosphonium bromide (12.7 g, produced by Tokyo Chemical Industry Co., Ltd.), and 3.75 mol of an aqueous HCl solution (40 mL) were added, and the reactor was purged with Ar gas for 15 minutes. Subsequently, the mixture solution was stirred in an oil bath (115° C.) to start the reaction. Twenty five hours after the start of the reaction, stirring was stopped, and the reactor was removed from the oil bath to terminate the reaction.

NMR measurement was performed on reaction solutions of Example 2 and Comparative Example 2, and also on 1-octene used as the raw material. From the results, the amounts of 1-octene and 2-chlorooctane in terms of % by weight contained in the reaction solutions were determined for each reaction time. The results are shown in Table 3.

TABLE 3

|  | Example 2 | | Comparative Example 2 | |
| --- | --- | --- | --- | --- |
|  | 1-octene (wt %) | 2-chlorooctane (wt %) | 1-octene (wt %) | 2-chlorooctane (wt %) |
| Material | 100 | 0 | 100 | 0 |
| Reaction 25 hours later | 5 | 90 | 30 | 62 |

It could be confirmed from Table 3 that, in Example 2 in which irradiation with a 1580 to 1680 cm$^{-1}$ infrared ray having a peak at 1630 cm$^{-1}$ was performed and Comparative Example 2 in which such irradiation was not performed, the reaction from 1-octene to 2-chlorooctane proceeded faster in Example 2. This result showed that a reaction product could be efficiently obtained by allowing the organic synthesis reaction to proceed while irradiating the starting material with an infrared ray having a peak at the target wavelength.

The examples described above pose no limitations on the present invention.

The present application claims priority from Japanese Patent Application No. 2016-152522 filed on Aug. 3, 2016, the entire contents of which are incorporated herein by reference.

What is claimed is:

1. A method for producing a reaction product, with which the reaction product is obtained from a starting material through a particular organic synthesis reaction, the method comprising:
    (a) a step of setting a target wavelength to a peak wavelength of a reaction region in intramolecular reactions, intermolecular reactions between identical molecules, or intermolecular reactions between dissimilar molecules involved in the organic synthesis reaction in an infrared absorption spectrum of the starting material;
    (b) a step of preparing an infrared heater that emits an infrared ray having a peak, which has a full width at half maximum of 1.0 μm or less at the target wavelength from a structure constituted by a metal pattern, a dielectric layer, and a metal substrate stacked in this order from an outer side toward an inner side; and
    (c) a step of obtaining the reaction product by allowing the organic synthesis reaction to proceed while the infrared ray having a peak, which has a full width at half maximum of 1.0 μm or less at the target wavelength, is being applied to the reaction region in intramolecular reactions, intermolecular reactions between identical molecules, or intermolecular reactions between dissimilar molecules of the starting material from the infrared heater.

2. The method for producing a reaction product according to claim 1,
    wherein the metal pattern is constituted by metal electrodes identical in size and shape arranged on the dielectric layer so as to be equally spaced from one another, and
    wherein a peak wavelength of an infrared ray emitted from the infrared heater changes depending on a width of the metal electrodes.

3. The method for producing a reaction product according to claim 1,
    wherein the target wavelength is set within a range of wavelength of 2.5 μm or more and 25 μm or less.

4. The method for producing a reaction product according to claim 1, wherein the target wavelength is set to a peak wavelength of a reaction region involved in stretching vibration.

5. A method for producing a reaction product, with which the reaction product is obtained from a starting material through a particular organic synthesis reaction, the method comprising:
    (a) a step of setting a target wavelength to a peak wavelength of a reaction region in intramolecular reactions, intermolecular reactions between identical molecules, or intermolecular reactions between dissimilar molecules involved in the organic synthesis reaction in an infrared absorption spectrum of the starting material;
    (b) a step of preparing an infrared heater that emits an infrared ray having a peak, which has a full width at half maximum of 1.0 μm or less at the target wavelength from a structure constituted by a heating element and a plate-shaped member disposed below the heating element; and
    (c) a step of obtaining the reaction product by allowing the organic synthesis reaction to proceed while the infrared ray having a peak, which has a full width at half maximum of 1.0 μm at the target wavelength, is being applied to the reaction region in intramolecular reactions, intermolecular reactions between identical molecules, or intermolecular reactions between dissimilar molecules of the starting material from the infrared heater.

6. The method for producing a reaction product according to claim 5,
    wherein the plate-shaped member comprises a metal pattern that is constituted by metal electrodes identical in size and shape arranged on a dielectric layer so as to be equally spaced from one another, and
    wherein a peak wavelength of an infrared ray emitted from the infrared heater changes depending on a width of the metal electrodes.

7. The method for producing a reaction product according to claim 5,
    wherein the target wavelength is set within a range of wavelength of 2.5 μm or more and 25 μm or less.

8. The method for producing a reaction product according to claim 5, wherein the target wavelength is set to a peak wavelength of a reaction region involved in stretching vibration.

* * * * *